United States Patent [19]

Schaefer et al.

[11] 4,384,141
[45] May 17, 1983

[54] PREPARATION OF α-BROMOACETOPHENONE-OXIME-ETHERS

[75] Inventors: Peter Schaefer, Kirchheim; Dietrich Mangold, Neckargemuend, both of Fed. Rep. of Germany

[73] Assignee: BASF Aktiengesellschaft, Ludwigshafen, Fed. Rep. of Germany

[21] Appl. No.: 318,573

[22] Filed: Nov. 5, 1981

[30] Foreign Application Priority Data

Nov. 26, 1980 [DE] Fed. Rep. of Germany ....... 3044564

[51] Int. Cl.³ .......................................... C07C 131/00
[52] U.S. Cl. ..................................... 564/256; 260/694
[58] Field of Search ....................... 564/256, 253, 259

[56] References Cited

U.S. PATENT DOCUMENTS 4,293,715 10/1971 Kramer ................................ 564/256

OTHER PUBLICATIONS

Chu, Sou-yie et al., J. Org. Chem., vol. 36 (1971), pp. 3467–3469.
Finar, I. L., "Organic Chemistry", vol. 2 (1963), p. 92, Longmans, Publ.
Houben–Weyl, "Methoden der organischen Chemie", Band V/4 (1960), p. 214, Georg Thieme, Publ.

*Primary Examiner*—Natalie Trousof
*Assistant Examiner*—L. Hendriksen
*Attorney, Agent, or Firm*—John H. Shurtleff

[57] ABSTRACT

α-Bromoacetophenone-oxime-ethers are prepared by reacting acetophenone-oxime-ethers with a brominating agent at from 20° to 100° C., in the absence of light.

The α-bromoacetophenone-oxime-ethers obtained are valuable starting materials for the preparation of drugs, dyes and pesticides.

14 Claims, No Drawings

PREPARATION OF α-BROMOACETOPHENONE-OXIME-ETHERS

The present invention relates to a novel process for the preparation of α-bromoacetophenone-oxime-ethers by reacting acetophenone-oxime-ethers with a brominating agent at from 20° to 100° C., in the absence of light.

J. Org. Chem. 36 (1971), 3,467–3,469 discloses that ketoxime-O-ethers or aldoxime-O-ethers can be brominated in the α-position by reaction with N-bromosuccinimide under exposure to light. However, only O-alkyl-oxime-ethers are obtainable by this method, since, if other substituents, for example benzyl, are present on the oxime oxygen atom, bromine attacks the substituents, and mixtures of compounds are formed. The publication mentioned emphasizes the importance of good illumination (ultraviolet light).

We have found that α-bromoacetophenone-oxime-ethers of the formula

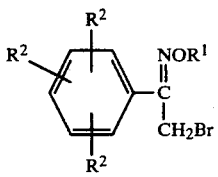

where $R^1$ is an acetylenically unsaturated aliphatic or an araliphatic radical and $R^2$ is hydrogen, halogen or an aliphatic radical, the individual $R^2$'s being identical or different, are obtained in an advantageous manner when an acetophenone-oxime-ether of the formula

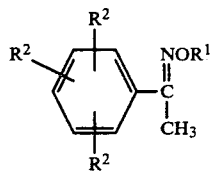

where $R^1$ and $R^2$ have the above meanings, is reacted with a brominating agent at from 20° to 100° C., in the absence of light.

If 2,4-dichloroacetophenone-oxime-O-benzyl-ether and bromine are used, the reaction can be represented by the following equation:

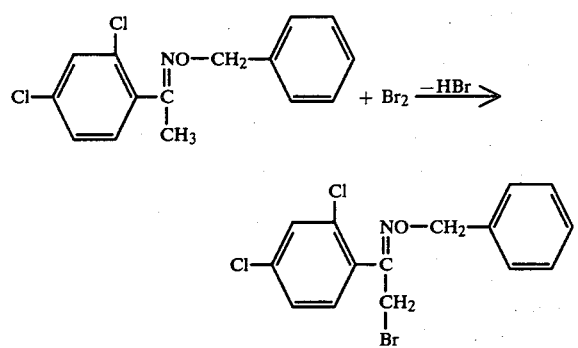

Compared to the prior art, the process according to the invention surprisingly gives α-bromoacetophenone-oxime-ethers more simply and more economically, in better yield, higher space-time yield and greater purity, in particular on an industrial scale and in continuous operation.

It is surprising that under the process conditions according to the invention, the acetophenone-oxime-ethers II are brominated stereoselectively at the —$CH_3$ group. Unexpectedly, there is no attack on the $R^1$ group, even though the aromatic radical or carbon-carbon triple bond activates the hydrogen atoms of this moiety of the molecule (Houben-Weyl, Methoden der Organischen Chemie, Volume 5/4, pages 153–163). Furthermore, the hydrogen bromide formed during the main reaction does not cause any cleavage reactions.

The process according to the invention has a number of advantages. It permits, inter alia, the preparation of α-bromoketoxime-ethers whose substituents carry activated hydrogen atoms on the oxime oxygen. Under the process conditions according to the invention, these hydrogen atoms do not undergo replacement by bromine. Further, elementary bromine can be employed as the halogenating agent. Free radical initiators, or illumination, are not needed. All these advantageous results are surprising in view of the prior art. It would furthermore have been expected that dispensing with the use of a powerful light source when carrying out a bromination would lead to reduced yields or even to the reaction not proceeding at all.

The starting material II can be reacted with a stoichiometric amount or excess of the brominating agent; preferably with from 1 to 1.25, especially from 1 to 1.1, moles thereof per mole of II. Preferred starting materials II and accordingly preferred end products I are those where $R^1$ is alkynyl of 2 to 20, especially of 2 to 8, carbon atoms or is an aralkyl of 7 to 12 carbon atoms, and $R^2$ is hydrogen, bromine, iodine or, in particular, chlorine or alkyl of 1 to 6 carbon atoms, the individual $R^2$'s being identical or different. The above radicals can be additionally substituted by groups and atoms which are inert under the reaction conditions, for example by chlorine, bromine or alkyl of 1 to 4 carbon atoms.

Accordingly, examples of suitable starting materials II are the benzyl-, ethynyl-, propynyl-, 1-butynyl-, pentynyl-, propargyl-, 2-butynyl-, phenylethyl- and phenylpropyl-O-ether of substituted or unsubstituted acetophenone-oxime. Preferred starting materials are 2,4-dichloroacetophenone-oxime-O-propargyl-ether and 2,4-dichloroacetophenone-oxime-O-benzyl-ether.

Suitable brominating agents are, in general, bromine itself or compounds which form bromine under the reaction conditions, as a rule bromides. Advantageously, a bromide together with an oxidizing agent and an acid is used as the bromine-forming mixture; equally, an oxidizing agent and hydrogen bromide can be used, the latter advantageously in the form of an aqueous hydrogen bromide solution. The bromides used are preferably the alkaline earth metal salts and, in particular, the alkali metal salts, eg. calcium bromide, magnesium bromide, lithium bromide and especially sodium bromide and potassium bromide.

Advantageous oxidizing agents include chromium compounds, eg. potassium bichromate, sodium bichromate, ammonium bichromate, chromic acid and chromyl chloride; permanganates, eg. potassium permanganate, or $MnO_2$; nitric acid, and its salts, eg. sodium nitrate, silver nitrate, potassium nitrate, sodium nitrate, lithium nitrate, calcium nitrate, magnesium nitrate, nickel nitrate, chromium nitrate, copper nitrate, cobalt nitrate, cerium nitrate, thorium nitrate, bismuth nitrate, iron nitrate and mercury nitrate; metal oxides, eg. PbO, PbO$_2$, CuO, Os$_5$O$_4$, RuO$_4$, HgO, SeO$_2$ and Ag$_2$O; metal salts, such as iron-III chloride, iron-III cyanides, eg. potassium hexacyanoferrate, copper chloride, copper sulfate, copper acetate, lead tetraacetate, manganese tetraacetate, mercury-II acetate and silver chlorate; organic oxidizing agents, eg. chloranil, potassium nitrosodisulfonate and p-nitrosodimethylaniline; and oxygen and ozone. The oxidizing agents are advantageously employed in a ratio of from 0.001 to 0.5, preferably from 0.05 to 0.1, mole per mole of starting material II or, if oxygen is used as the oxidizing agent, in a ratio of from 0.05 to 2 moles per mole of starting material II. In a preferred embodiment, the halogenation is carried out in the presence of hydrogen peroxide as the oxidizing agent, advantageously with from 1 to 1.5, especially from 1 to 1.25, equivalents of hydrogen peroxide, based on starting material II. The hydrogen peroxide is advantageously used in the form of an aqueous solution whose strength is from 5 to 60, preferably from 10 to 30, percent by weight. Compounds which form hydrogen peroxide under the reaction conditions may also be used, for example inorganic or organic peroxo compounds, eg. sodium peroxide, potassium peroxide, magnesium peroxide, calcium peroxide, zinc peroxide, barium peroxide; hydroperoxides, eg. NaOOH.0.5 H$_2$O$_2$ and NH$_4$OOH; corresponding hydrates, eg. CaO$_2$.8-H$_2$O, and peroxohydrates, eg. BaO$_2$.H$_2$O$_2$ and BaO$_2$.2-H$_2$O$_2$; peroxodisulfuric acid and peroxomonosulfuric acid and their salts, eg. sodium peroxodisulfate, potassium peroxodisulfate and ammonium peroxodisulfate; peroxocarbonates, eg. sodium peroxocarbonate and calcium peroxocarbonate; and peroxophosphates, eg. potassium peroxodiphosphate.

Further suitable brominating agents are bromides of phosphoric acid, phosphorous acid, carbonic acid, oxalic acid, sulfuric acid and sulfurous acid, eg. sulfuryl bromide, thionyl bromide, phosphorus pentabromide, phosphorus tribromide, phosphorus oxybromide, oxalyl bromide, bromosulfonic acid and carbonyl bromide. In certain cases, halogen oxyacids, their anhydrides or their salts, eg. hypobromous acid, bromic acid and their sodium and potassium salts, can also be used. Further suitable brominating agents are N-bromine derivatives of organic acid amides, eg. bromo-N-succinimide, bromo-N-glutarimide, bromo-N-adipimide, bromosulfamic acid, bromosulfamide and the bromine derivatives of cyanuric acid and of 5,5-dimethylhydantoin. Where appropriate, the above bromine compounds can also be used conjointly with oxidizing agents and/or with free bromine.

Preferred brominating agents are bromosuccinimide, N-bromoacetamide, perbromides, eg. pyridinium perbromide, 2,4,4,6-tetrabromocyclohexa-2,5-dienone, 5,5-dibromo-2,2-dimethyl-4,6-dioxo-1,3-dioxane and especially bromine itself.

The reaction is carried out at from 20° to 100° C., preferably from 35° to 90° C., especially from 40° to 70° C., under reduced pressure, atmospheric pressure or superatmospheric pressure, batchwise or continuously. Advantageously, an organic solvent which is inert under the reaction conditions is used. Examples of suitable solvents are aromatic hydrocarbons, eg. toluene, ethylbenzene, o-, m- and p-xylene, isopropylbenzene and methylnaphthalene; halohydrocarbons, especially bromohydrocarbons and chlorohydrocarbons, eg. tetrachloroethylene, 1,1,2,2- and 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, bromoform, ethyl iodide, propyl iodide, chloronaphthalene, dichloronaphthalene, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane, and mixtures of the above. Advantageously, the solvent is used in an amount of from 80 to 10,000 percent by weight, preferably from 100 to 600 percent by weight, based on starting material II.

The reaction can be carried out as follows: a mixture of the starting material II and the brominating agent is left at the reaction temperature for from 1 to 12 hours. The end product is then isolated in a conventional manner, for example by washing the mixture and then subjecting it to fractional distillation.

The α-bromoacetophenone-oxime-ethers I, thus obtained, are valuable starting materials for the preparation of drugs, dyes and pesticides. Thus, they are valuable intermediates for the systhesis of fungicidally active α-azolylacetophenone-oxime-ethers of the formula III

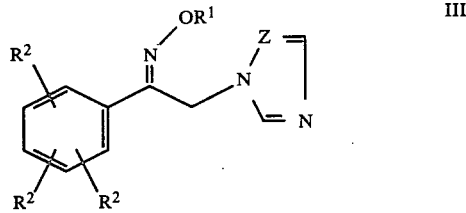

where Z is CH or N and R$^1$ and R$^2$ have the meanings given for formula I. The fungicidally active compounds of the formula III are a subject of German Laid-Open Applications DOS 2,723,942 and DOS 2,657,578. The reaction of the corresponding phenacyl chlorides or bromides (haloketones) with the azoles, according to German Laid-Open Application DOS 2,431,407, and subsequent oximation and etherification, is proposed in the said DOS's for their preparation. Compared to this method, the reaction of the easily obtained α-bromoacetophenone-oxime-ethers of the formula I with the azoles gives more satisfactory yields, and furthermore the α-bromoacetophenone-oxime-ethers do not require additional purification, ie. they can be reacted, as obtained, with 1,2,4-triazole or imidazole to give the fungicidally active compounds of the formula III. The reaction is carried out at from 20° to 120° C., in an inert, organic solvent. Suitable solvents are alcohols, eg. methanol and ethanol, nitriles, eg. acetonitrile, amides, eg. dimethylformamide and dimethylacetamide, and mixtures of these solvents.

To bind the hydrogen bromide formed in the reaction, a basic compound is added to the reaction mixture, for example an alkali metal carbonate, eg. sodium carbonate or potassium carbonate, an alcoholate, eg. sodium methylate or sodium ethylate, sodium hydride, butyllithium, an amine, eg. diisopropylethylamine, or a lithium amide, eg. lithium diisopropylamide. It is also possible to use an excess of imidazole or of 1,2,4-triazole to bind the hydrogen bromide.

The reactants can be employed in stoichiometric amounts, but preferably the 1,2,4-triazole or imidazole is used in an excess of from 20 to 200 mole percent.

Preparation of
α-(1,2,4-triazolyl)-acetophenone-oxime-O-(4-chlorobenzyl)-ether nitrate.

A mixture of 0.2 mole of 1,2,4-triazole and 0.2 mole of sodium carbonate in 200 ml of ethanol is raised to the reflux temperature and a solution of 0.1 mole of α-bromoacetophenone-oxime-O-(4-chlorobenzyl)-ether in 50 ml of ethanol is then added. The mixture is refluxed for three hours and then evaporated down, and the residue is taken up in a mixture of methylene chloride and water. The organic phase is mixed with water and nitric acid is added dropwise, whilst cooling. The nitrate which precipitates is filtered off and dried. 15 g (=39% yield) of α-(1,2,4-triazolyl)-acetophenone-oxime-O-(4-chlorobenzyl)-ether nitrate are obtained; metling point 130° C., with decomposition.

In the Examples which follow, parts are by weight, and bear the same relation to parts by volume as that of the kilogram to the liter.

EXAMPLE 1

14.7 parts of 2,4-dichloroacetophenone-oxime-O-benzyl-ether are introduced into 100 parts of carbon tetrachloride and a solution of 8 parts of bromine in 50 parts of carbon tetrachloride is added at 50° C., in the absence of light. After the mixture has been stirred for 2 hours, it is washed twice with 100 parts of water and once with 100 parts of sodium bicarbonate solution and dried over potassium carbonate. Fractional distillation gives 13.1 parts of α-bromo-2,4-dichloroacetophenone-oxime-O-benzyl-ether (70% of theory); boiling point 120° C./6.10$^{-5}$ mbar.

EXAMPLE 2

15.2 parts of 4-bromoacetophenone-oxime-O-benzyl-ether are introduced into 100 parts of methylene chloride and a solution of 8 parts of bromine in 50 parts of methylene chloride is added at 40° C., in the absence of light. After the mixture has been stirred for 4 hours, it is worked up similarly to Example 1. 13.7 parts of α-4-dibromoacetophenone-oxime-O-benzyl-ether (72% of theory) are obtained; boiling point 110° C/8.10$^{-5}$ mbar.

We claim:

1. A process for the preparation of α-bromoacetophenone-oxime-ethers of the formula

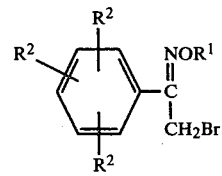

where $R^1$ is an araliphatic radical and $R^2$ is hydrogen, halogen or an aliphatic radical, the individual $R^2$'s being identical or different, which comprises: reacting an acetophenone-oxime-ether of the formula

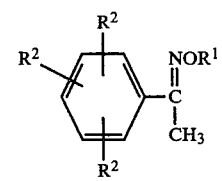

where $R^1$ and $R^2$ have the above meanings, with a brominating agent at from 20° to 100° C., in the absence of light.

2. A process as claimed in claim 1, wherein the reaction is carried out with from 1 to 1.25 moles of brominating agent per mole of starting material II.

3. A process as claimed in claim 1, wherein the reaction is carried out with a bromide in the presence of an ozidizing agent and an acid.

4. A process as claimed in claim 1, wherein the reaction is carried out with from 0.001 to 0.5 mole of oxidizing agent per mole of starting material II.

5. A process as claimed in claim 1, wherein the reaction is carried out with from 0.05 to 2 moles of oxygen, as the oxidizing agent, per mole of starting material II.

6. A process as claimed in claim 1, wherein the reaction is carried out with hydrogen peroxide as the oxidizing agent, used in an amount of from 1 to 1.5 equivalents, based on starting material II.

7. A process as claimed in claim 1, wherein the reaction is carried out with bromosuccinimide, N-bromoacetamide, perbromides, 2,4,4,6-tetrabromocyclohexa-2,5-dienone, 5,5-dibromo-2,2-dimethyl-4,6-dioxo-1,3-dioxane and/or bromine.

8. A process as claimed in claim 1, wherein the reaction is carried out at from 35° to 90° C.

9. A process as claimed in claim 1, wherein the reaction is carried out at from 40° to 70° C.

10. A process as claimed in claim 1, wherein the reaction is carried out in an organic solvent which is inert under the reaction conditions.

11. A process as claimed in claim 1 wherein $R^1$ is aralkyl of 7 to 12 carbon atoms and $R^2$ is selected from the group consisting of hydrogen, bromine, iodine, chlorine and alkyl of 1 to 6 carbon atoms.

12. A process as claimed in claim 11 wherein $R^1$ is benzyl.

13. A process as claimed in claim 11 wherein the reaction is carried out at from 35° to 90° C.

14. A process as claimed in claim 11 wherein the reaction is carried out in an organic solvent which is inert under the reaction conditions.

* * * * *